United States Patent [19]

Prass

[11] Patent Number: 4,892,105
[45] Date of Patent: Jan. 9, 1990

[54] ELECTRICAL STIMULUS PROBE

[75] Inventor: Richard L. Prass, Lakewood, Ohio

[73] Assignee: The Cleveland Clinic Foundation, Cleveland, Ohio

[21] Appl. No.: 144,642

[22] Filed: Jan. 11, 1988

Related U.S. Application Data

[63] Continuation of Ser. No. 845,848, Mar. 28, 1986, abandoned.

[51] Int. Cl.$^4$ ............................................. A61N 1/32
[52] U.S. Cl. .................................... 128/741; 128/784
[58] Field of Search ............ 128/734, 741, 744, 303.1, 128/13, 303.18–303.19, 639, 642, 800–801, 783–784

[56] References Cited

U.S. PATENT DOCUMENTS

| | | | |
|---|---|---|---|
| 1,717,480 | 6/1929 | Wappler | 128/303.18 |
| 2,110,735 | 3/1938 | Marton | 128/303.18 |
| 2,516,882 | 8/1950 | Kalom | 128/303.18 X |
| 2,994,324 | 8/1961 | Lemos | 128/801 X |
| 3,035,580 | 5/1962 | Guiorguiev | 128/303.18 |
| 3,060,923 | 10/1962 | Reiner . | |
| 3,087,486 | 4/1963 | Kilpatrick | 128/642 |
| 3,147,750 | 9/1964 | Fry | 128/734 X |
| 3,580,242 | 5/1971 | Croix | 128/642 |
| 3,651,812 | 3/1972 | Samuels | 128/303.18 |
| 3,662,744 | 5/1972 | Low et al. | 128/744 |
| 3,830,226 | 8/1974 | Staub et al. | 128/741 |
| 3,957,036 | 5/1976 | Normann . | |
| 4,099,519 | 7/1978 | Warren | 128/741 |
| 4,141,365 | 2/1979 | Fischell et al. | 128/642 |
| 4,155,353 | 5/1979 | Rea et al. | 128/642 |
| 4,308,012 | 12/1981 | Tamler et al. | 128/741 X |
| 4,402,323 | 9/1983 | White | 128/642 |
| 4,483,338 | 11/1984 | Bloom et al. | 128/303.18 X |
| 4,515,168 | 5/1985 | Chester et al. | 128/741 |

OTHER PUBLICATIONS

Kartush et al.; "Intraoperative Facial Nerve Monitoring: A Comparison of Stimulating Electrodes"; *Laryngoscope* 95, 12-1985, pp. 1536–1540.

Basmajian & Stecko, "A New Bipolar Electrode for Electromyography", J. Appl. Physiol 17:849, 1962.

Moller & Jannetta, "Preservation of Facial Function During Removal of Acourstic Neuromas", J. Neurosurg. 61:757–760, 1984.

Babin, Ryu & McCabe, "Bipolar Localization of the Facial Nerve in the Internal Auditory Canal", Disorders of the Facial Nerve . . . 1982.

*Primary Examiner*—Angela D. Sykes
*Attorney, Agent, or Firm*—D. Peter Hochberg; Mark Kusner; Louis J. Weisz

[57] ABSTRACT

A hand-held instrument for electrically stimulating tissue of a living body in the presence of body fluid comprising an elongated, relatively fine, electrically conductive wire having a planar conductive surface generally transverse to the axis thereof at one end. Insulation carried flush to the tip of the wire is provided along the peripheral surface of the wire to prevent shunting of electrical stimulus by the body fluid through such surface. A tube encases the insulated wire in a manner such that a portion of the wire is external to the tube and is adjustable relative thereto.

14 Claims, 1 Drawing Sheet

ELECTRICAL STIMULUS PROBE

This is a continuation of copending application Ser. No. 845,848 filed on Mar. 28, 1986 now abandoned.

FIELD OF THE INVENTION

The present invention relates to surgical apparatus and more particularly to a hand held electrical stimulus probe for use as an intraoperative aid in defining the course of neural structures. The invention is particularly applicable for use in acoustic monitoring of facial electromyogram (EMG) activity during acoustic neuroma surgery and will be described with reference thereto, although it will be appreciated that the invention has broader applications and can be used in other neural monitoring procedures.

BACKGROUND OF THE INVENTION

Posterior fossa tumors are tumors located at the posterior fossa region of the skull, i.e. the inner surface of the base of the skull. Cranial nerve involvement is common with posterior fossa tumors over a certain size. Acoustic neuromas are most common of the posterior fossa tumors and can involve hearing loss. Because of their location and neural involvement, surgery to correct such tumors is difficult. Despite advancements in diagnosis, microsurgical techniques, and neurotological techniques which enable more positive anatomical identification of facial nerves, loss of facial nerve function following acoustic neuroma resection is a significant risk. In this respect, nerves are very delicate, and even the best and most experienced surgeons, using the most sophisticated equipment known heretofore, encounter a considerable hazard that a nerve will be bruised, stretched or even severed during an operation.

Recent studies have shown that preservation of the facial nerve during acoustic neuroma resection may be enhanced by the use of intraoperative electrical stimulation to assist in locating nerves. Very broadly stated, this procedure involves inserting recording electrodes directly within cranial muscles controlled by the nerve of interest. An electrical probe is then applied near the area where the subject nerve is believed to be located. If the probe contacts, or is reasonably near the nerve, the signal applied thereto is transmitted through the nerve to excite the related muscles. Excitement of the muscles causes an electrical impulse to be generated therein, which impulse is transferred to the recording electrodes which provide, by suitable means, an indication to the surgeon as to the location of the nerve.

While intraoperative electrical stimulation has been of benefit in the localization and preservation of facial nerves during various surgical procedures, the accuracy and reliability of such stimulation depends upon eliminating sources of false stimulation. A major source of false stimulation is the shunting of the electrical stimulus away from the intended area through body fluids. In this respect, during acoustic neuroma surgery the surgical area is variably bathed in cerebrospinal fluid (CSF), which is a clear, colorless body fluid containing electrolytes and is capable of conducting electrical current. Heretofore, stimulus probes were comprised of standard bare wire or tapered metal rods which were touched to the area to be stimulated. These probes allow electrical contact with the electrolyte fluid such that the electrical stimulus may spread along parallel channels. Such spread of the stimulus reduces electrical current flow through the point of contact with the tissue intended for stimulation, which may result in false stimulation and thus affect the accuracy of the procedure. It has been suggested that one solution to this problem is to increase the intensity level of the electrical stimulus such that the neural response to stimulation occurs despite such shunting. Increased stimulus levels however increase the possibility of tissue damage. Further, the stimulus may spread through inactive tissue and reach active tissue at a level sufficient to produce a false response which would likewise affect the accuracy of the procedure.

These and other problems are overcome by a preferred embodiment of the present invention which provides an electrical stimulus probe which reduces shunting of the electrical stimulus through body fluids and provides a higher degree of spatial selectivity.

SUMMARY OF THE INVENTION

In accordance with an embodiment of the present invention, there is provided a hand-held instrument for use in electrically stimulating tissue of a living body. The instrument is comprised of handle means having an elongated, generally flexible, electrically conductive element extending therefrom, which conductive element includes an outer conductive surface along the length thereof and a planar conductive surface at the end thereof. The outer conductive surface of the element is electrically insulated such that electrical stimulation can only be transmitted through the planar conductive surface. The conductive element includes means associated therewith to maintain the orientation of the element along a predetermined path, and is electrically connected to a source of electrical stimulation energy.

Importantly, the construction of the present invention provides insulation carried flush to the tissue-engaging tip end of the instrument. This construction, i.e. the flushtip, substantially reduces the spread of the electrical stimulus through body fluids by reducing exposure of electrically conductive surface area to such fluids. Eliminating this shunting effect allows greater reliability and spatial selectivity of electrical stimulation.

In accordance with another aspect of the present invention, the tissue engaging tip end of the electrically conductive element is adjustable relative to the element's orientation along the predetermined path wherein the tip end may be adjusted by the surgeon to allow flush contact with the tissue to be stimulated.

In accordance with still another aspect of the present invention, the electrically conductive element and the means for orienting the element along a predetermined path comprise a probe which is detachable from the handle means. In this respect, a probe may be detached from the handle means and replaced by another new (fresh) probe or by a probe having different electrical characteristics and/or configuration commensurate to the needs of the surgeon.

In this respect, preliminary findings have shown that a flush-tip probe according to the present invention, as compared with "bare-tip" probes known heretofore, requires less current to achieve a given response when constant-current stimulation is used in the presence of cerebrospinal fluid (CSF). Likewise, when constant voltage stimulation is used in the presence of CSF, a flush-tip probe generally requires the least voltage to achieve a given response level. In other words, a flushtip probe requires less power (current x voltage) to achieve a given response level, which is important in that, as set forth above, high power levels increase the possibility of tissue damage.

Also important, is that the flush-tip configuration finds advantageous application in both monopolar and bipolar probes. The difference between a monopolar and bipolar probe pertains to the location of the anode electrode relative to the cathode (the more active stimulus) electrode. A monopolar probe is generally the cathode electrode in an arrangement wherein the anode (generally acting as a ground) is located away therefrom. A bipolar configuration has the anode placed in proximity to the cathode. Placement of the anode near the cathode has been advocated because it tends to confine the electrical stimulus to a smaller area. It is believed that such confinement may improve spatial resolution and may decrease injury potential. On the other hand, placement of the anode at a distance from the cathode is favored because it is less bulky and less affected by the orientation of the electrodes relative to that of the neural structure to be stimulated. Regardless of the anode placement however, the flush-tip construction of the cathode and/or the anode increases the reliability and accuracy of electrical stimulation in an intraoperative setting.

An object of the present invention is to provide an instrument for electrically stimulating tissue in a living body for use as an intraoperative aid in locating and defining the course of neural structures.

Another object of the present invention is to provide an instrument for electrically stimulating tissue in a living body, which instrument offers a more accurate and reliable stimulation by overcoming the shunting effect caused by body fluid in the operating field.

Another object of the present invention is to provide an instrument as described above which can be utilized with either constant-voltage or constant current sources and requires minimum power to achieve a given response level.

A still further object of the present invention is to provide an instrument as described above wherein power delivered to the tissues may be maintained within a narrow and acceptable range under a wide range of shunt conditions.

A still further object of the present invention is to provide an instrument as described above which may be used in a monopolar or a bipolar configuration.

A still further object of the present invention is to provide an instrument as described above which includes a tissue engaging tip end which is adjustable relative the orientation of the instrument.

An even further object of the present invention is to provide an instrument as described above which includes a needle-like probe which is detachable from a handle portion.

These and other objects and advantages will become apparent from the following description of a preferred embodiment thereof taken together with the accompanying drawings.

BRIEF DESCRIPTION OF THE DRAWINGS

The invention may take form in certain parts and arrangement of parts, a preferred embodiment of which will be described in detail in this specification and illustrated in the accompanying drawings which form a part thereof and wherein.

DESCRIPTION OF PREFERRED EMBODIMENT

Figures 1, 2, 3:
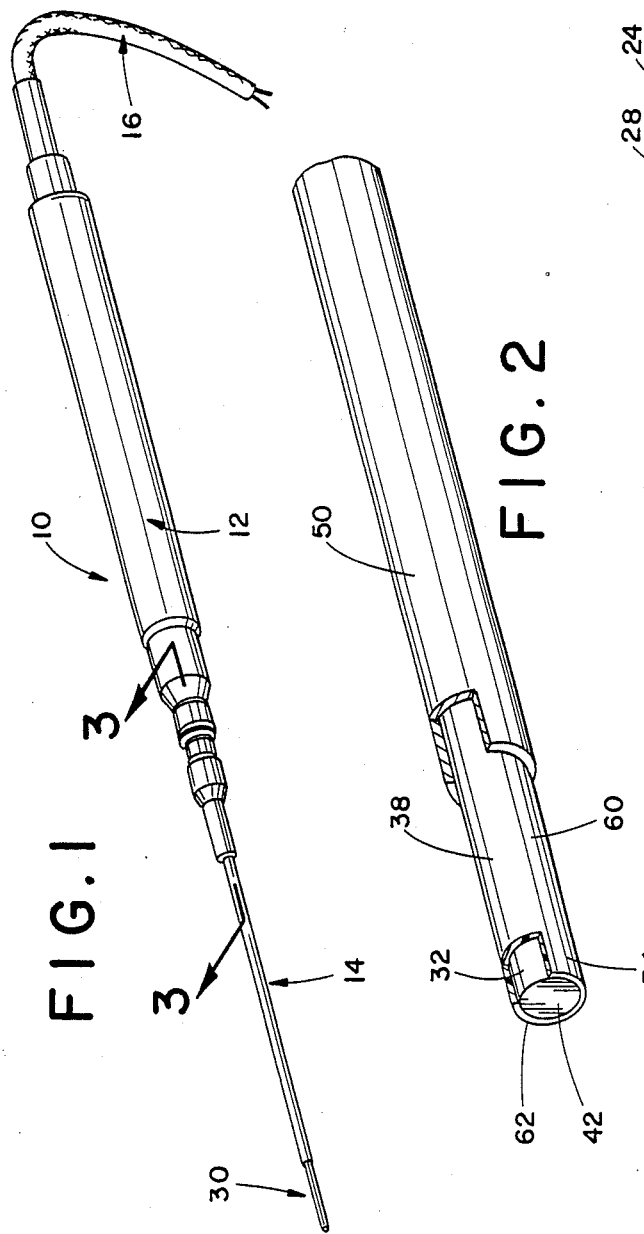
FIG. 1 is a perspective view showing a hand-held instrument in accordance with the present invention for electrically stimulating tissue in a living body.
FIG. 2 is an enlarged, partially sectioned view showing the tissue engaging tip end of the instrument shown in FIG. 1.
FIG. 3 is an enlarged sectional view taken along lines 3—3 of FIG. 1 illustrating the detachable connection between the probe portion and handle portion of the instrument.

Referring now to the drawings wherein the showings are for the purpose of illustrating a preferred embodiment of the invention, and not for the purpose of limiting same, FIG. 1 shows a hand-held instrument 10 for electrically stimulating tissue of a living body. Instrument 10 is a monopolar stimulus instrument, however it will be appreciated that the novel features of the present invention are not limited to such a structure but also find equal application in a bipolar configuration. Instrument 10 is basically comprised of a handle portion 12, a probe portion 14 which is preferably aligned with handle portion 12 and detachable therefrom, and lead 16 for connecting instrument 10 to a source of electrical stimulus.

Handle portion 12, in and of itself forms no part of the present invention, and therefor will not be described in great detail. Generally, handle portion 12 includes an cylindrical body 20 of non-conductive material extending along an axis A having a female connector 22 at one end thereof. Female connector 22 is electrically joined to lead 16 in a manner as conventionally known. A covering or casing 24 of resilient insulating material is provided along body 20. Covering 24 includes a collar 26 on the probe end of body 20, which collar 26 defines an opening 28.

Probe portion 12 is relatively long, having a needle-like configuration, and is generally comprised of a flexible electrically conductive element 30 having an outer surface 32 and distal ends 34, 36, as seen in FIGS. 2 and 3 respectively. A sheath 38 of insulating material is provided over outer surface 32. As seen in FIG. 3, end 36 is connected to a male connector 40 which is dimensioned to be received in axial alignment and in electrically conductive fashion in female connector 22 of handle portion 12. End 34 of element 30, which is the tissue engaging end of probe portion 14, includes a planar surface 42 generally perpendicular to the longitudinal axis thereof.

According to the preferred embodiment, electrically conductive element 30 and sheath 38 are comprised of a length of insulated No. 24 silver-plated copper wire. As will be appreciated, the present invention is not limited to a specific wire guage or length. Basically, the dimensions of the wire effect the impedance of the instrument. In general, the smaller the wire the greater the impedance. In this respect, as set forth above, the present invention provides an instrument wherein the probe may be detached from the handle and exchanged for a new probe having a different diameter and/or configuration. Thus enabling the surgeon to replace probes to achieve an optimum response while maintaining a narrow power range. Removal of the probe is simple and quick, and is accomplished by merely separating the probe axially from the handle. A new probe may then be inserted. Male connector 40 is dimensioned to snuggly fit, and to be retained in, female connector 22.

To provide rigidity and to maintain a directional orientation for probe portion 14, a thin-walled metal tube 50 encases a major portion of element 30 as best seen in FIG. 3. Tube 50 is maintained a short distance from male connector 40 to ensure no electrical contact exists therebetween. In this respect, a non-conductive, organic resin 52 may be dabbed where element 30 and male connector 40 are joined. Resin 52 generally coats exposed portion of element 30 and maintains a non-conductive spacing between tube 50 and male connector 40. A sleeve 54 of heatshrinkable material is provided over portions of tube 50 and male connector 40. Sleeve 54 is operative to seal the connection between element 30 and male connector 40, and at the same time to generally align tube 50 with respect to male connector 40. In addition, sleeve 54 is provided to interact with collar 26 to environmentally seal the connection between connectors 22, 40. To this end, sleeve 54 is dimensioned to be positioned in opening 28 and operatively interact with collar 26 of covering 24 to generally provide a seal therebetween. In this respect, the embodiment has been described as including a single sleeve 54. It will of course be appreciated that a plurality of sleeves, layered on top of each other could be used to achieve the same results without deviating from the present invention.

Referring now to the tissue engaging end of probe portion 14, as seen in the drawings, a portion 60 of element 30 extends a predetermined distance beyond the end of tube 50. Because element 30 is comprised of a flexible small diameter wire, portion 60 of element 30 is adjustable relative to the axis of tube 50. In this respect, end 34 of element 30 may be bent or adjusted by the surgeon to facilitate positioning thereof so as to allow flush contact with the tissue to be stimulated. Importantly, insulation 38 is maintained on the outer surface of portion 60. As best seen in FIG. 2, insulation 38 is carried flush to the tip of conductive element 30. The end of insulation 38 defines a generally annular surface 62 which is coplanar with surface 42 of element 30. According to the preferred embodiment, tissue engaging end 34 is prepared by cutting element 30 and sheath 38 transversely with a scalpel under microscopic vision or its equivalent.

When used in a surgical setting, only the planar surface 42 of electrically conductive element 30 is exposed to conduct electrical stimulus. In this respect, the flush-tips configuration prevents shunting of stimulus through body fluids by eliminating conductive surfaces exposed to such fluids. As set forth above, preliminary findings show that a flush-tip probe, compared to a bare-wire probe, required less power (current x voltage) when either constant-current or constant voltage stimulation was used in the presence of cerebrospinal fluid (CSF). Importantly, a decreased stimulation level reduces the possibility of tissue damage. In addition, elimination of shunting allows greater reliability and spatial selectivity of electrical stimulation. The flush-tip construction of the present invention increases the reliability and accuracy of electrical stimulation in an intraoperative setting.

Referring more specifically to the embodiment heretofore described, the overall length of probe portion 14 is approximately 4 inches wherein the male connector portion comprises approximately 1 inch thereof. The diameter of the insulated wire described in the preferred embodiment is approximately 0.035 inches in diameter. Tube 50, which is comprised of a material called Bakelite, has an outer diameter of approximately 0.050 inches. These dimensions are provided not as limitations to the present invention, but rather to portray the long needle-like configuration of probe portion 14. Importantly, this (relatively long, slender probe) configuration provides the surgeon with a view of the surgical field unobscured by the instrument's handle portion or his own hand. Further, the adjustable tip end and rigid tubular portion enable the surgeon to easily manipulate and "feel" the tissue engaging tip end of the probe. This permits more accurate positioning of the probe and flush contact with the tissue to be stimulated. These advantages being in addition to the reduced shunting and detachable probe feature described above.

Although a preferred embodiment of the invention has been described, modifications and alterations will appear to those skilled in the art upon reading and understanding the specification. For example, small diameter plastic tubing, instead of metal tubing may be provided to align element 30. Likewise, as set forth above, the present invention may be adapted to a bipolar configuration. It is intended that all such modifications and alterations be included insofar as they come within the scope of the claims or the equivalents thereof.

Having thus described the invention, the following is claimed:

1. A hand held instrument for electrically stimulating exposed, subcutaneous tissue of a living body comprising:
    an elongated, relatively flexible, electrically conductive wire element including a handle end and a tissue engaging end having a planar surface generally transverse to the axis of said wire element, said wire having sufficient rigidity to generally resist bending when in operable contact with said exposed subcutaneous tissue;
    a tube encasing said wire element and orienting said wire element along a predetermined path, wherein a predetermined portion of said wire element is external of said tube and is adjustable relative thereto;
    handle means disposed on the handle end of said wire element for manipulating said instrument;
    means for connecting said wire element to a source of electrical stimulation energy; and
    a sheath electrically insulating the peripheral surface along the length of said wire element wherein only said planar surface at the tissue engaging end thereof transmits electrical stimulus to said tissue when said wire element is positioned thereagainst.

2. An instrument as defined in claim 1 wherein said electrically conductive wire element and said tube are detachable from said handle means.

3. An instrument as defined in claim 1 wherein said tube is comprised of thin-walled metal tubing of cylindrical cross-section, and said insulating sheath is disposed between said wire element and said tube.

4. An instrument as defined in claim 1 wherein said instrument is monopolar.

5. A hand-held instrument for electrically stimulating exposed, subcutaneous tissue of a living body comprising:
    handle means for manipulating said instrument;
    an elongated, relatively flexible, electrically conductive element extending from said handle means having an outer conductive surface extending along the length thereof and a planar conductive surface at the end thereof, said element having sufficient rigidity to generally resist bending when in operable contact with said exposed subcutaneous tissue;

means electrically insulating said outer conductive surface;

means for maintaining said element aligned along a predetermined path, and means for connecting said element to an electrical stimulation energy, said electrically conductive element and said maintaining means being detachable from said handle means.

6. An instrument as defined in claim 5 wherein, said electrically conductive element is a solid metal wire, said maintaining means is a thin-walled tube encasing a portion of said wire, and, said insulating means is disposed between said tube and said wire.

7. An electrical stimulus probe for electrically stimulating exposed, subcutaneous tissue of a living body, comprising, an elongated, relatively flexible, electrically conductive wire element having an outer conductive surface and a planar conductive surface at one end thereof, said wire element having sufficient rigidity to resist bending when in operable contact with said exposed subcutaneous tissue.

a sheath electrically insulating said outer conductive surface, a thin-walled tube encasing said wire element along a major portion thereof, said wire element including a portion external of said tube which is adjustable relative thereto, and means connecting said wire element to a source of electrical stimulation energy.

8. An electrical probe as defined in claim 7 wherein said connecting means is comprised of handle means attachable/detachable from said probe.

9. An electrical probe as defined in claim 7 wherein said conductive wire element has a diameter of approximately 0.035 inches in diameter.

10. An electrical probe as defined in claim 7 wherein said tube orients said conductive wire element along a predetermined path relative a handle attachable to said probe.

11. An electrical probe as defined in claim 7 wherein said probe has a long needle-like configuration.

12. An electrical stimulus probe for electrically stimulating exposed, subcutaneous tissue of a living body, comprising;

an elongated electrically conductive element having an outer conductive surface and a planar conductive surface at one end thereof, an axially extending, generally rigid section comprising a major portion of said elongated element, a relatively flexible section at said one end of said element, said flexible section movable in relation to said rigid section yet having sufficient rigidity to resist movement when in operable contact with said exposed subcutaneous tissue, a sheath electrically insulating said outer conductive surface of said conductive element wherein only said planar conductive surface is exposed to said subcutaneous tissue, and means for connecting said wire element to a source of electrical stimulation energy.

13. A probe as defined in claim 12 wherein said rigid section includes tubular means encasing said conductive element.

14. A probe as defined in claim 12 wherein said conductive element has a generally circular cross-section and said flexible section has a diameter smaller than said rigid section.

* * * * *